(12) United States Patent
Seeber et al.

(10) Patent No.: US 8,580,982 B2
(45) Date of Patent: Nov. 12, 2013

(54) USE OF STRUCTURED CATALYST BEDS FOR PREPARING ETHYLENE OXIDE

(76) Inventors: Georg Seeber, Lambsheim (DE); Torsten Mäurer, Lambsheim (DE); Gerhard Theis, Maxdorf (DE); Dieter Köffer, Birkenau (DE); Frank Rosowski, Mannheim (DE)

( * ) Notice: Subject to any disclaimer, the term of this patent is extended or adjusted under 35 U.S.C. 154(b) by 18 days.

(21) Appl. No.: 13/376,879

(22) PCT Filed: Jun. 9, 2010

(86) PCT No.: PCT/EP2010/058065
§ 371 (c)(1),
(2), (4) Date: Dec. 8, 2011

(87) PCT Pub. No.: WO2010/142714
PCT Pub. Date: Dec. 16, 2010

(65) Prior Publication Data
US 2012/0077998 A1    Mar. 29, 2012

(30) Foreign Application Priority Data
Jun. 9, 2009 (EP) .................................... 09162254

(51) Int. Cl.
C07D 301/03    (2006.01)

(52) U.S. Cl.
USPC ........................................................ 549/536

(58) Field of Classification Search
USPC ........................................................ 549/536
See application file for complete search history.

(56) References Cited

U.S. PATENT DOCUMENTS

| | | | |
|---|---|---|---|
| 4,324,699 A | 4/1982 | Mross et al. | |
| 4,389,338 A | 6/1983 | Mitsuhata et al. | |
| 4,732,918 A | 3/1988 | Lohmueller et al. | |
| 4,774,222 A | 9/1988 | Rashkin | |
| 5,011,809 A | 4/1991 | Herzog et al. | |
| 5,173,469 A | 12/1992 | Wunde | |

FOREIGN PATENT DOCUMENTS

| | | |
|---|---|---|
| CA | 1026763 A1 | 2/1978 |
| CA | 2089982 A1 | 8/1993 |
| DE | 23 00 512 A1 | 7/1973 |
| DE | 24 54 972 A1 | 6/1975 |
| DE | 25 21 906 A1 | 12/1975 |
| DE | 27 53 359 A1 | 6/1979 |
| DE | 31 50 205 A1 | 8/1982 |
| DE | 33 21 895 A1 | 12/1983 |
| DE | 34 14 717 A1 | 10/1985 |
| DE | 25 60 684 C2 | 10/1989 |
| EP | 0011356 A1 | 5/1980 |
| EP | 14 457 A2 | 8/1980 |
| EP | 0082609 A1 | 6/1983 |
| EP | 0085237 A1 | 8/1983 |
| EP | 0172565 A2 | 2/1986 |
| EP | 0229465 A1 | 7/1987 |
| EP | 0266015 A1 | 5/1988 |
| EP | 0339748 A2 | 11/1989 |
| EP | 0357293 A1 | 3/1990 |
| EP | 384 312 A1 | 8/1990 |
| EP | 0428845 A1 | 5/1991 |
| EP | 0557833 A1 | 9/1993 |
| GB | 1413251 A | 11/1975 |
| GB | 1512625 A | 6/1978 |
| JP | 56005471 A | 1/1981 |
| WO | WO-2004/078711 A2 | 9/2004 |

OTHER PUBLICATIONS

International Search Report for PCT/EP2010/058065, mailing date Oct. 4, 2010.
Office Action dated Aug. 6, 2013 from Chinese Patent Office regarding corresponding Chinese Application No. 201080025705.9.

*Primary Examiner* — Taylor Victor Oh
(74) *Attorney, Agent, or Firm* — Novak Druce Connolly Bove + Quigg LLP

(57) ABSTRACT

The present invention relates to a process for preparing ethylene oxide by reaction of ethylene with oxygen in the presence of at least one silver-comprising catalyst, wherein the reaction takes place in a reactor which has a catalyst packed bed having at least two zones (i) and (ii) and the silver content of the catalyst in zone (i) is lower than the silver content of the catalyst in zone (ii). The catalyst packed bed preferably has a further zone (a) with which the reaction mixture comes into contact before the zones (i) and (ii). According to the invention, the silver content of the catalyst in the zone (a) is higher than the silver content of the catalyst in zone (i).

9 Claims, No Drawings

USE OF STRUCTURED CATALYST BEDS FOR PREPARING ETHYLENE OXIDE

CROSS-REFERENCE TO RELATED APPLICATIONS

This application is a national stage application (under 35 U.S.C. §371) of PCT/EP2010/058065, filed Jun. 9, 2010, which claims benefit of European application 09162254.8, filed Jun. 9, 2009, the contents of each of which are incorporated herein by reference in their entireties.

FIELD OF THE INVENTION

The present invention relates to a process for preparing ethylene oxide by reaction of ethylene with oxygen in the presence of at least one silver-comprising catalyst, wherein the reaction takes place in a reactor which has a catalyst packed bed having at least two zones (i) and (ii) and the silver content of the catalyst in zone (i) is lower than the silver content of the catalyst in zone (ii).

BACKGROUND

Ethylene oxide, an important basic chemical, is prepared industrially by oxidation of ethylene by means of oxygen in the presence of silver-comprising catalysts. For this purpose, use is usually made of supported catalysts to which the catalytically active, metallic silver has been applied by means of a suitable method.

The preparation of ethylene oxide is usually carried out using a supported silver catalyst (Ag on $Al_2O_3$) which has a silver concentration of 15-30% by weight of silver. The catalyst can comprise further active metals in addition to silver.

Processes which use structured catalyst beds which have gradients of, for example, promoters and comprise catalyst layers of differing activity or selectivity are known from the prior art.

JP-A 56005471 describes, for example, a process for preparing ethylene oxide in which alkali metal-comprising silver catalysts are used which are loaded with different amounts of alkali metal along the length of the catalyst bed so that an alkali metal concentration gradient is present along the bed. At the upper end of the catalyst bed, i.e. at the point at which the reaction gas enters, the alkali metal content of the silver catalyst should, according to this document, be lower than at the other end of the catalyst bed, i.e. where the reaction gas leaves the reactor. Since alkali metal doping of the silver catalyst results in a decrease in the activity and an increase in the selectivity of the catalyst for the formation of ethylene oxide, the reaction gas mixture comes into contact with increasingly selective and decreasingly active silver catalyst on passing through the reactor.

EP 0 557 833 A1 discloses a combination of high-selectivity and high-activity catalysts in a structured catalyst bed. A description is given of a process for preparing ethylene oxide by oxidation of ethylene by means of oxygen in the presence of silver- and promoter-comprising catalysts, with at least two silver catalysts of differing selectivity and activity being used in a combined catalyst bed.

EP 0 428 845 A1 discloses a catalyst which has a silver gradient within a single shaped catalyst body.

WO 2004/078711 discloses a process for preparing ethylene oxide, which is operated at reduced $CO_2$ concentration. High-selectivity and high-activity structured catalyst beds are used.

In the scientific publication "Oxidation of ethylene to ethylene oxide: catalyst deactivation in an industrial run", Montrasi et al., Applied Catalysis (1983), 5 (3), 359-369, describe a study on the deactivation of industrial EO catalysts along the reactor tube.

In the processes known from the prior art, the activity of the catalyst continually decreases over the entire time of operation of the catalyst in production operation. After an optimization phase, the catalyst reaches its maximum/optimum selectivity which then decreases again during further operation. To maintain a particular production output (work rate), the temperature is therefore usually increased during production operation. A disadvantage of this mode of operation is the continual temperature increase which is necessary for maintaining the production output in order to compensate for the continual decrease in the selectivity of the catalyst after the selectivity maximum has been reached.

An objective of catalyst research is to keep the operating temperature of the catalyst, which is an influencing factor on the deactivation, over a period as long as possible so low that the catalyst achieves the highest possible selectivities over a period of time as long as possible.

BRIEF SUMMARY

Proceeding from this prior art, it was an object of the present invention to provide a process for the industrial preparation of ethylene oxide which displays a high long-term stability of the catalyst.

According to the invention, this object is achieved by a process for preparing ethylene oxide by reaction of ethylene with oxygen in the presence of at least one silver-comprising catalyst, wherein the reaction takes place in a reactor which has a catalyst bed having at least two zones (i) and (ii) and the silver content of the catalyst in zone (i) is lower than the silver content of the catalyst in zone (ii).

According to the invention, the reaction of ethylene with oxygen takes place in the presence of at least one silver-comprising catalyst in a reactor which has a catalyst bed having at least two zones (i) and (ii). According to the invention, the zones (i) and (ii) comprise a silver-comprising catalyst. Here, the silver content of the catalyst in zone (i) is lower than the silver content of the catalyst in zone (ii).

The catalyst packed bed can, according to the invention, also comprise further zones (iii), (iv), (v), (vi) and so forth, which comprise a silver-comprising catalyst. Here, the silver content of the catalyst in a zone (x) is preferably in each case higher than the silver content of the catalyst in the zone (x-1). The catalyst packed bed preferably has the zones (i) and (ii).

For the purposes of the present invention, the individual zones of the catalyst packed bed are arranged in the reactor so that the zone (i) is located closer to the reactor inlet than the zone (ii) which is in turn located closer to the reactor inlet than the zone (iii), and so forth. Accordingly, the reaction mixture flows through zone (i) during the reaction before zone (ii) and this in turn before zone (iii), and so forth. Thus, a zone (x-1) is each flown through before a zone (x).

DETAILED DESCRIPTION OF THE PREFERRED EMBODIMENTS

It has been found that the use of a multizone packed bed of a silver-comprising catalyst with an increasing silver concentration of the catalyst (silver gradient) along the catalyst packed bed (in the flow direction of the gas stream) makes it possible to increase or stabilize the activity of the structured catalyst bed compared to the 100% pure catalysts. For the purposes of the present invention, a silver gradient is a continuous or discontinuous change in the silver concentration.

If two or more catalysts are combined in a structured catalyst bed, an improvement is achieved when the concentration of silver increases along the gas stream in the reactor. In the case of a catalyst bed comprising the zones (i) and (ii), the selectivity is proportional to the catalyst having the lower silver content comprised in zone (i), with the activity surprisingly being determined by the catalyst comprised in zone (ii) of the catalyst packed bed. Thus, depending on the catalyst used, only 50%, for example, of zone (ii) in the catalyst bed is sufficient to achieve the same, high activity of the 100% pure catalyst packed bed comprising the same catalyst. The presence of zone (i) likewise results in better selectivity compared to the 100% pure catalyst bed composed of zone (ii). The use of structured catalyst packed beds in the process of the invention therefore gives a significant increase in activity.

Of course, it is also possible to use various mixtures of silver catalysts in combined catalyst beds according to the invention. The beds of silver catalysts combined according to the invention can, for example, be produced so that, in the simplest case, two or more zones of the various catalysts are located above one another in a catalyst tube.

Thus, according to the invention, the reaction mixture comes into contact with zone (i) and the catalyst comprised therein during the reaction before it comes into contact with zone (ii) and the catalyst comprised therein.

The present invention therefore provides, in a further embodiment, a process for preparing ethylene oxide by reaction of ethylene with oxygen in the presence of at least one silver-comprising catalyst as described above, wherein the reaction mixture comes into contact with zone (i) before it comes into contact with zone (ii).

For the purposes of the present invention, preference is given to each of the zones (i) and (ii) of the catalyst packed bed making up at least 10% of the total catalyst packed bed, particularly preferably at least 20% of the total catalyst bed, in particular at least 30% of the total catalyst bed.

The present invention therefore provides, in a further embodiment, a process for preparing ethylene oxide by reaction of ethylene with oxygen in the presence of at least one silver-comprising catalyst as described above, wherein zone (i) and zone (ii) each make up at least 10% of the total catalyst packed bed.

For the purposes of the present invention, the zones (i) and (ii) can make up approximately equal proportions of the total packed catalyst bed. However, it is likewise possible for the zones (i) and (ii) to make up different proportions of the total catalyst bed.

For example, in an embodiment of the present invention, zone (i) can make up from 40 to 70% of the total catalyst bed, preferably from 45 to 65% of the total catalyst bed, in particular from 50 to 60% of the total catalyst bed.

The present invention therefore provides, in a further embodiment, a process for preparing ethylene oxide by reaction of ethylene with oxygen in the presence of at least one silver-comprising catalyst as described above, wherein zone (i) makes up from 40 to 70% of the total catalyst bed.

In a further embodiment of the present invention, zone (ii) can, for example, make up from 20 to 60% of the total catalyst packed bed, preferably from 25 to 50% of the total catalyst packed bed, in particular from 30 to 40% of the total catalyst packed bed.

The present invention therefore provides, according to a further embodiment, a process for preparing ethylene oxide by reaction of ethylene with oxygen in the presence of at least one silver-comprising catalyst as described above, wherein zone (ii) makes up from 20 to 60% of the total catalyst packed bed.

Apart from the zones (i), (ii), (iii), and so forth, as described above, the catalyst packed bed can have further zones. These zones can comprise a silver-comprising catalyst. However, it is likewise possible for the catalyst packed bed to have further zones which do not comprise any silver-comprising catalyst, i.e., for example, only an inert material.

In an embodiment of the present invention, the catalyst packed bed comprises, in addition to the zones (i), (ii), (iii), and so forth, preferably in addition to the zones (i) and (ii), a preceding zone (a) comprising a silver-comprising catalyst, with this zone being closer to the reactor inlet than the zone (i) and the silver content of the catalyst in the zone (a) being higher than the silver content of the catalyst in the zone (i).

Accordingly, the zone (a) and the catalyst comprised therein comes into contact with the reaction mixture during the reaction before the reaction mixture comes into contact with the zone (i) and the catalyst comprised therein.

The present invention therefore provides, in a further embodiment, a process for preparing ethylene oxide by reaction of ethylene with oxygen in the presence of at least one silver-comprising catalyst as described above, wherein the catalyst packed bed has a further zone (a) with which the reaction mixture comes into contact before the zones (i) and (ii) and the silver content of the catalyst in the zone (a) is higher than the silver content of the catalyst in zone (i).

This preceding zone (a) can serve as "guard bed" in order to protect the later zones, in particular zone (i), since deactivation takes place particularly in the front gas inlet region of the reactor during operation of an EO production plant.

Zone (a) preferably makes up, according to the invention, not more than 10% of the total catalyst packed bed, in particular not more than 8% of the total catalyst bed, particularly preferably not more than 6% of the total catalyst packed bed.

For the purposes of the present invention, the catalyst bed preferably does not have any further zones comprising a silver-comprising catalyst in addition to the zones (a), (i) and (ii). However, the catalyst packed bed can, in this embodiment, have further zones which do not comprise a silver-comprising catalyst.

The present invention therefore provides, in a further embodiment, a process for preparing ethylene oxide by reaction of ethylene with oxygen in the presence of at least one silver-comprising catalyst as described above, wherein zone (a) makes up not more than 10% of the total catalyst packed bed.

According to the invention, preference is given to the silver content of the catalyst in the individual zones not changing over the running time of the process, i.e. aging of the catalyst preferably not resulting in a change in the silver content.

The present invention therefore provides, in a further embodiment, a process for preparing ethylene oxide by reaction of ethylene with oxygen in the presence of at least one silver-comprising catalyst as described above, wherein the gradient of the silver content of the catalyst in the zones of the catalyst bed is present over the entire running time of the process.

According to the invention, the catalyst comprised in the individual zones of the catalyst packed bed differs in terms of its silver content. It is possible, within the scope of the present invention, for the silver content of the catalyst in a zone (x-1) to be from 5 to 15% lower than the silver content of the catalyst in the zone (x). The silver content of the catalyst in zone (i) is therefore preferably from 5 to 15% lower than the silver content of the catalyst in zone (ii); in particular, the silver content of the catalyst in zone (i) is from 8 to 12% by weight lower than the silver content of the catalyst in zone (ii), with particular preference being given to the silver content of the catalyst in zone (i) being from 9 to 11% by weight lower than the silver content of the catalyst in zone (ii).

The present invention therefore provides, in a further embodiment, a process for preparing ethylene oxide by reaction of ethylene with oxygen in the presence of at least one silver-comprising catalyst as described above, wherein the silver content of the catalyst in zone (i) is from 5 to 15% by weight lower than the silver content of the catalyst in zone (ii).

For example, the catalyst comprised in zone (i) of the catalyst packed bed has a silver content of from 10 to 20% by weight, preferably from 12 to 18% by weight, in particular 13% by weight, 14% by weight, 15% by weight, 16% by weight or 17% by weight.

The catalyst comprised in zone (ii) of the catalyst packed bed has, for example, a silver content of from 20 to 40% by weight, preferably from 22 to 30% by weight, in particular 23% by weight, 24% by weight, 25% by weight, 26% by weight, 27% by weight, 28% by weight or 29% by weight.

According to the invention, the catalyst comprised in zone (a) can, for example, have the same silver content as the catalyst comprised in zone (ii). Accordingly, the catalyst comprised in zone (ii) of the catalyst packed bed has, for example, a silver content of from 20 to 40% by weight, preferably from 22 to 30% by weight, in particular 23% by weight, 24% by weight, 25% by weight, 26% by weight, 27% by weight, 28% by weight or 29% by weight.

The catalyst comprised in the individual zones of the catalyst packed bed can, according to the invention, comprise further active metals and promoters in addition to silver.

In the process of the invention, it is possible to use all silver-comprising supported catalysts suitable for preparing ethylene oxide from ethylene and oxygen as silver catalysts. As support material, it is in principle possible to employ any porous material which is stable under the conditions of the ethylene oxide synthesis, for example activated carbon, aluminum oxides, titanium, zirconium or silicon dioxides or other ceramic compositions.

The geometric shape of the support particles is generally of minor importance; however, the support particles should advantageously have shapes which allow unhindered diffusion of the reaction gases at a very large part of the external and internal surface of the support particles which is coated with the catalytically active silver particles which may optionally be doped with additives.

The catalytically active constituents of the silver catalysts as are employed in the process of the invention, i.e. silver and any dopants added, can be applied by all impregnation and deposition processes of the prior art in order to produce silver catalysts for the preparation of ethylene oxide, with these processes being able to comprise one or more impregnation and calcination steps. Mention may be made by way of example of the production processes for silver catalysts as are disclosed in DE-A 23 00 512, DE-A 25 21 906, EP-A 14 457, EP-A 85 237, EP-A 384 312, DE-A 24 54 972, DE-A 33 21 895, EP-A 229 465, DE-A 31 50 205, EP-A 172 565 and EP-A 357 293. The doping of the silver catalysts which can be used in the process of the invention with additives which, for example, influence the activity, selectivity and operating life of the silver catalysts, known as promoters, is in principle not subject to any restrictions, i.e. it is possible to use all promoters of the prior art for doping the silver catalysts. As promoters of this type, particular mention may be made of alkali metal and alkaline earth metal hydroxides or salts and also compounds of the elements of transition groups 6 and 7 of the Periodic Table (notation in accordance with the IUPAC proposal of 1985), in particular compounds of the elements tungsten, molybdenum and/or rhenium.

The anions of the salts of the promoters are likewise not subject to any restrictions; for example, all halides, in particular fluoride, chloride, carboxylates, nitrate, sulfur-comprising anions such as sulfate or sulfide, phosphates, cyanide, hydroxide, carbonates or anions of heteropolyacids, in particular heteropolyacids of elements of transition groups 6 and 7 of the Periodic Table, particularly preferably anions of heteropolyacids of tungsten, molybdenum and/or rhenium, can be anions of these salts.

As examples of promoter-doped silver catalysts which can be used in the process of the invention, mention may be made of the silver catalysts of DE-A 23 00 512, DE-A 25 21 906, EP-A 14 457, DE-A 24 54 972, EP-A 172 565, EP-A 357 293, EP-A 266 015, EP-A 11 356, EPA 85 237, DE-A 25 60 684 and DE-A 27 53 359.

The catalyst preferably comprises rhenium and at least one further metal as promoter in addition to silver. The present invention therefore provides, in a further embodiment, a process for preparing ethylene oxide by reaction of ethylene with oxygen in the presence of a silver-comprising catalyst as described above, wherein at least one of the catalysts used in the zones comprises rhenium.

According to the invention, it is also possible for a plurality or all of the catalysts used in the zones to comprise rhenium.

The silver catalysts disclosed in the documents mentioned by way of example above, having the contents of silver and promoters indicated therein and produced by the impregnation, drying, silver decomposition and calcination processes indicated therein, can all be used with good success in the process of the invention. It is therefore not the type of the particular catalysts used which is critical for the success of the process of the invention but rather solely the measure of using combined beds of catalysts which differ in terms of the silver content. Only by means of this measure is it possible to achieve the abovementioned advantages, e.g. the lengthening of the operating life of the silver catalysts concerned.

Ethylene oxide can be produced by direct oxidation of ethylene by means of oxygen using methods which are conventional per se with the aid of the catalyst beds of silver catalysts combined according to the invention. It is for this purpose possible to use all reactors which can be employed in the ethylene oxide production processes of the prior art, for example the externally cooled shell-and-tube reactors which are usually used industrially (cf. Ullmann's Encyclopedia of Industrial Chemistry; 5th Ed.; Vol. A10; pp. 117-135, 123-125; VCH Verlagsgesellschaft; Weinheim 1987) and also reactors having a loose catalyst bed and cooling tubes, for example the reactors as described in DE-A 34 14 717, EP-A 82 609 and EP-A 339 748. To produce the combined catalyst packed bed, the various catalysts are usually introduced in succession, in the desired order, into the reactor concerned.

To prepare ethylene oxide from ethylene and oxygen by means of the catalyst packed beds according to the invention, it is possible to work under conventional reaction conditions as are described, for example, in DE-A 25 21 906, EP-A 14 457, DE-A 23 00 512, EP-A 172 565, DE-A 24 54 972, EP-A 357 293, EP-A 266 015, EP-A 85 237, EP-A 82 609 and EP-A 339 748. Inert gases such as nitrogen or gases which are inert under the reaction conditions, e.g. steam, methane, and optionally reaction moderators (inhibitors), for example halogenated hydrocarbons such as ethyl chloride, vinyl chloride or 1,2-dichloroethane, can be additionally mixed into the reaction gas comprising ethylene and molecular oxygen. The oxygen content of the reaction gas is advantageously in a range in which no explosive gas mixtures are present. A suitable composition of the reaction gas for preparing ethylene oxide can, for example, comprise about 30% by volume of ethylene, about 7% by volume of oxygen, from 0.5 to 5 ppm of a chlorine-comprising reaction moderator such as ethyl chloride, vinyl chloride or dichloroethane, with the balance of the reaction gas generally being able to be composed of hydrocarbons such as methane or ethane or else inert gases such as nitrogen. In addition, the reaction gas can further comprise other substances such as water vapor, carbon dioxide or noble gases. The oxidation is generally carried out at temperatures of from 165 to 300° C.

The preparation of ethylene oxide from ethylene and oxygen can advantageously be carried out in a circulation process. Here, the reaction gas mixture is circulated through the reactor and after each pass the newly formed ethylene oxide and also by-products formed in the reaction are removed from the product gas stream which is, after supplementation with the required amounts of ethylene, oxygen and reaction moderators, recirculated to the reactor. The separation of the ethylene oxide from the product gas stream and the work-up thereof can be carried out by the customary methods of the prior art (cf. Ullmann's Encyclopedia of Industrial Chemistry; 5th Ed.; Vol. A10; pp. 117-135, 123-125; VCH Verlagsgesellschaft; Weinheim 1987).

The present invention is illustrated below with the aid of examples.

EXAMPLES

Catalyst A comprising 8.6% by weight of silver and catalyst B comprising 18.6% by weight of silver were used.

Composition of the catalysts:

| Composition: | Catalyst A | Catalyst B |
|---|---|---|
| Silver (% by weight) | 8.6 | 18.6 |
| Lithium (ppm by weight) | 190 | 190 |
| Sulfur (ppm by weight) | 14 | 14 |
| Tungsten (ppm by weight) | 200 | 200 |
| Cesium (ppm by weight) | 460 | 460 |
| Rhenium (ppm by weight) | 310 | 310 |

A porous aluminum oxide which can be obtained, for example, from Süd-Chemie, Noritake, CeramTec or Industriey Bitossi was used as support material for each of the catalysts A and B.

The catalysts A and B used were produced by customary methods as disclosed, for example, in EP-A 266 015.

A cylindrical double-walled reactor made of stainless steel of DIN type 1.4541 was used as tube reactor. The internal diameter of the tube bounded by the inner wall (the reaction space) was 6 mm. The wall thickness of the inner wall was 1 mm. The distance between the outer wall and the inner wall was 3.5 mm. The wall thickness of the outer wall was 3.2 mm.

A heat transfer oil AP 100 Silikonöl from Wacker Chemie AG, Munich, was passed (at a pumping rate of about 15 l/min) as temperature-control medium through the intermediate space between the two walls. The length of the tube reactor was 2200 mm. The heat transfer oil was fed in at an entry temperature $T_w^{in}$ at the lower end of the tube reactor and flowed upward from the bottom to the top where it flowed out of the space between the walls.

From the bottom upward, the reaction space was charged as follows:

an after-bed of inert steatite spheres (steatite C220 from CeramTec) having a sphere diameter of from 1.0 to 1.6 mm in an amount of 9 g; the bed length was about 21.2 cm;

a packed bed of 32 g of crushed catalysts having a particle size of from 0.6 to 0.9 mm; the bed length was about 110 cm; and a preliminary-bed of inert steatite spheres (steatite C220 from CeramTec) having a sphere diameter of from 1.0 to 1.6 mm in an amount of 29 g; the bed length was about 70.7 cm.

The reaction space was empty over its remaining length.

A reaction gas starting mixture having the following composition:

35% by volume of ethylene,
7% by volume of molecular oxygen,
1% by volume of carbon dioxide,
0.15% by volume of water,
from 2 to 6 ppm by volume of ethyl chloride (moderator) and
methane as balance to 100% by volume was passed through the reaction space from the bottom upward.

The entry pressure of the reaction gas mixture on entering the reaction space was 16 bar absolute. The reaction gas starting mixture was preheated to a temperature of 130° C. The space velocity of the reaction gas starting mixture through the about 110 cm long crushed catalyst bed was 4750 $h^{-1}$. $T_w^{in}$ was selected and continually adjusted so that the ethylene oxide content of the reaction gas mixture on leaving the reaction space was always 2.7% by volume. The ethyl chloride content of the reaction gas starting mixture was increased over the running time so that the maximum selectivity of ethylene oxide target product formation was ensured at all times during operation.

After a running-in phase of 300 hours of operation, the following experimental results were obtained:

E1: 100% of catalyst A:
$T_w^{in}$=238.4° C.;
ethyl chloride content: 3.0 ppm by volume;
$S^{eth}$=85.9 mol %.

E2: 100% of catalyst B:
$T_w^{in}$=230.9° C.;
ethyl chloride content: 2.6 ppm by volume;
$S^{eth}$=84.3 mol %.

E3: 33% by weight of catalyst A (zone (i))/67% by weight of catalyst B (zone (ii)):
$T_w^{in}$=232.6° C.;
ethyl chloride content: 2.6 ppm by volume;
$S^{eth}$=85.3 mol %.

It could be seen that a weight ratio of the catalysts having different silver compositions of 1 (lower proportion of silver): 2 (higher proportion of silver) within the catalyst packed bed led, compared to catalyst B having the higher silver content, to a virtually identical activity and a significantly increased selectivity.

The invention claimed is:

1. A process for preparing ethylene oxide by reaction of ethylene with oxygen in the presence of at least one silver-comprising catalyst, wherein the reaction takes place in a reactor which has a catalyst packed bed having at least two zones (i) and (ii) and the silver content of the catalyst in zone (i) is lower than the silver content of the catalyst in zone (ii), and wherein the reaction mixture comes into contact with zone (i) before it comes into contact with zone (ii).

2. The process according to claim 1, wherein zone (i) and zone (ii) each make up at least 10% of the total catalyst packed bed.

3. The process according to claim 1, wherein zone (i) makes up from 40 to 70% of the total catalyst packed bed.

4. The process according to claim 1, wherein zone (ii) makes up from 20 to 60% of the total catalyst packed bed.

5. The process according to claim 1, wherein the catalyst packed bed has a further zone (a) with which the reaction mixture comes into contact before the zones (i) and (ii) and the silver content of the catalyst in the zone (a) is higher than the silver content of the catalyst in zone (i).

6. The process according to claim 5, wherein zone (a) makes up not more than 10% of the total catalyst packed bed.

7. The process according to claim 1, wherein the gradient of the silver content of the catalyst in the zones of the catalyst packed bed is present over the entire running time of the process.

8. The process according to claim 1, wherein the silver content of the catalyst in zone (i) is from 5 to 15% lower than the silver content of the catalyst in zone (ii).

9. The process according to claim 1, wherein at least one of the catalysts used in the zones comprises rhenium.

\* \* \* \* \*